(12) United States Patent
Al-Saeedi

(10) Patent No.: US 8,668,900 B2
(45) Date of Patent: Mar. 11, 2014

(54) CANCER-IMAGING AGENT AND METHOD OF RADIOIMAGING USING THE SAME

(75) Inventor: Fatma Jassab Faleh Marzooq Al-Saeedi, Safat (KW)

(73) Assignee: Kuwait University, Safat (KW)

( * ) Notice: Subject to any disclaimer, the term of this patent is extended or adjusted under 35 U.S.C. 154(b) by 635 days.

(21) Appl. No.: 13/028,047

(22) Filed: Feb. 15, 2011

(65) Prior Publication Data

US 2012/0207674 A1 Aug. 16, 2012

(51) Int. Cl.
*A61K 51/04* (2006.01)
*A61K 51/00* (2006.01)

(52) U.S. Cl.
USPC ....... 424/1.65; 424/1.73; 424/1.81; 424/1.85; 424/1.89

(58) Field of Classification Search
USPC .................... 424/1.65, 1.73, 1.81, 1.85, 1.89
See application file for complete search history.

(56) References Cited

U.S. PATENT DOCUMENTS

| | | | |
|---|---|---|---|
| 4,311,688 A | 1/1982 | Burchiel et al. | |
| 4,323,546 A | 4/1982 | Crockford et al. | |
| 4,478,815 A | 10/1984 | Burchiel et al. | |
| 6,010,679 A | 1/2000 | Edwards et al. | |
| 6,251,364 B1 | 6/2001 | Liu | |
| 7,289,840 B2 | 10/2007 | Norfray | |
| 7,459,141 B2 | 12/2008 | Park et al. | |
| 2003/0021749 A1* | 1/2003 | Yeung | 424/1.73 |
| 2009/0035201 A1 | 2/2009 | Park et al. | |

OTHER PUBLICATIONS

A. Mintz, L. Wang, and D.E. Pnde, "Comparison of radiolabeled choline and ethanolamine as probe for cancer detection," Cancer Biology & Therapy, 7:5, 742-747 May 2008.
C. Plathow and W.A. Weber, "Tumor Cell Metabolism Imaging," J.Nucl. Med., 49:43S-63S, 2008.

* cited by examiner

*Primary Examiner* — Michael G Hartley
*Assistant Examiner* — Jagadishwar Samala
(74) *Attorney, Agent, or Firm* — Richard C. Litman

(57) ABSTRACT

The cancer-imaging agent and method of radioimaging relates to the use of a radioimaging agent for the imaging increased choline uptake to detect cancerous tissue. The radioimaging agent includes choline or a pharmaceutically acceptable salt thereof labeled with technetium-99m. Preferably, the radioimaging agent is [methyl]-choline chloride labeled with $^{99m}TcO_4$, which carries technetium-99m. In use, a patient is administered an effective amount of the radioimaging agent by injection and then scanned with a radioimaging device. The radioimaging agent is used to image select soft tissues in the patient, such as the liver or gallbladder, the upper abdominal organs, or the like, and to detect increased choline uptake. Choline is known to accumulate in cancerous cells. Thus, the radioimaging agent is particularly effective in the detection of potentially cancerous tissues.

7 Claims, No Drawings

CANCER-IMAGING AGENT AND METHOD OF RADIOIMAGING USING THE SAME

BACKGROUND OF THE INVENTION

1. Field of the Invention

The present invention relates to radioisotopes and to radiographic techniques for detecting tumors, and particularly to a cancer-imaging agent and a method of radioimaging using the same, and more particularly to a method of detecting cancer by monitoring choline uptake using choline radiolabeled with technetium-99m ($^{99m}$Tc).

2. Description of the Related Art

There is presently great interest in methods for the noninvasive diagnosis of a variety of diseases, such as cancer. Radiopharmaceuticals formed from gamma-ray emitting radionuclide-labeled biologically active molecules are presently being studied. The biologically active molecules serve to localize the radionuclides at the sites of disease, and thus allow the sites to be visualized by gamma scintigraphy. The molecules are typically proteins, antibodies, antibody fragments, peptides or polypeptides, or peptidomimetics. The molecules interact with a receptor or binding site expressed at the sites of the disease, or with a receptor or binding site on an endogenous blood component, such as platelets and leukocytes, that accumulate at the sites. This interaction results in selective localization of a percentage of the injected radiopharmaceutical, while the remainder is cleared either through the renal or hepatobiliary systems.

The localized radiopharmaceutical is then imaged externally using gamma scintigraphy. The relative rates of sequestration, clearance and radionuclidic decay determine the ease of visualization, often expressed as the target-to-background ratio. Frequently, only certain portions of the biologically active molecules bind to the receptors. These portions are termed the recognition sequences or units.

There are two general methods for labeling biologically active molecules with radionuclides for use as radiopharmaceuticals, which are generally termed direct and indirect labeling. Direct labeling involves attaching the radionuclide to atoms on the biologically active molecule, while the indirect method involves attaching the radionuclide via a chelator. The chelator can either be attached to the biologically active molecule prior to reaction with the radionuclide, or the radionuclide-labeled chelator moiety can be attached to the biologically active molecule.

A number of radiopharmaceuticals formed from radionuclide-labeled proteins, antibodies or antibody fragments are being investigated. However few are actually being used clinically. The infrequent use of such compounds is due to a combination of factors that make developing these radiopharmaceuticals difficult, including problems with manufacturing and quality control, non-optimal sequestration and clearance rates, and the occurrence of antigenic or allergic responses to the radiopharmaceuticals. These problems are mainly due to the macromolecular nature of the proteins, antibodies and antibody fragments. Their high molecular weight makes direct chemical synthesis impractical. Therefore, they must be synthesized by recombinant or cloning techniques that typically give low yields and require extensive isolation and purification procedures. Their molecular weight can slow their rates of localization and preclude their clearance by an active elimination mechanism via the kidneys or liver, resulting in prolonged retention in the circulation, which causes a high background level during imaging. Also, the body's immune system tends to recognize more efficiently larger exogenous species.

The use of lower molecular weight molecules with known high-uptake rates, particularly in cancer cells, can alleviate these problems. It would be desirable to provide such a radioimaging agent. Thus, a cancer-imaging agent and method of radioimaging using the same solving the aforementioned problems is desired.

SUMMARY OF THE INVENTION

The cancer-imaging agent and method of radioimaging using the same relates to radioimaging and the usage of a radioimaging agent for the imaging of select soft tissues and the detection of potentially cancerous cells in the soft tissues. The radioimaging agent includes choline, or a pharmaceutically acceptable salt thereof, labeled with 99m-technetium ($^{99m}$Tc). Particularly, the radioimaging agent is formed by labeling choline, or a pharmaceutically acceptable salt thereof, with $^{99m}$Tc. Preferably, the radioimaging agent is [methyl]-choline chloride labeled with pertechnetate ion ($^{99m}$TcO$_4$—), which carries the $^{99m}$Tc isotope.

In use, a patient is administered an effective amount of the radioimaging agent and then scanned with a radioimaging device. The radioimaging agent is preferably injected into the patient in solution. The radioimaging agent is used to image select soft tissues in the patient, such as the liver or gallbladder, the upper abdominal organs, or the like, and to detect potentially cancerous cells in the scanned soft tissues. Choline is known to accumulate in cancerous cells. Thus, the radioimaging agent containing choline, or a pharmaceutically acceptable salt thereof, labeled with $^{99m}$TcO$_4$ is particularly effective in the detection of potentially cancerous cells in scanned soft tissues.

These and other features of the present invention will become readily apparent upon further review of the following specification.

DETAILED DESCRIPTION OF THE PREFERRED EMBODIMENTS

The cancer-imaging agent and method of radioimaging using the same relates to radioimaging and the use of a radioimaging agent for the imaging of select soft tissues and the detection of potentially cancerous cells in the soft tissues. The radioimaging agent includes choline, or a pharmaceutically acceptable salt thereof, labeled with $^{99m}$Tc. $^{99m}$Tc is a particularly common radionuclide utilized in radioimaging, and the radioimaging agent is preferably choline, or a pharmaceutically acceptable salt thereof, labeled with $^{99m}$TcO$_4$—, which carries the $^{99m}$Tc isotope. The radioimaging agent is preferably [methyl]-choline chloride labeled with $^{99m}$TcO$_4$—.

In use, a patient is administered an effective amount of the radioimaging agent and then scanned with a radioimaging device. The radioimaging agent is preferably injected into the patient in solution. The radioimaging agent is used to image select soft tissues in the patient, such as the liver or gallbladder, the upper abdominal organs, or the like, and to detect potentially cancerous cells in the scanned soft tissues. Choline is known to accumulate in cancerous cells. Thus, the radioimaging agent containing choline, or a pharmaceutically acceptable salt thereof, labeled with $^{99m}$Tc, is particularly effective in the detection of potentially cancerous cells in scanned soft tissues. The radioimaging agent is readily available, easy to manufacture, relatively inexpensive and non-harmful to the patient.

In experimental testing, [methyl]-choline chloride was labeled with $^{99m}$TcO$_4$. The biodistribution of the radioagent was investigated in adult male Sprague-Dawley (SD) rats weighing approximately 250±50 g. The SD rats were divided into two groups: a control group, which was administered sodium pertechnetate ($^{99m}TcO_4$); and the experimental group, which was administered $^{99m}$Tc-choline by injection. Each rat was subsequently anaesthetized prior to intravenous injections of 37 MBq of either $^{99m}TcO_4$ or $^{99m}$Tc-choline.

Dynamic imaging for 30 minutes for each group was implemented using a scintillation gamma camera. The biodistribution of $^{99m}$Tc-choline and $^{99m}TcO_4$ in the brains, lungs, kidneys, adrenal glands, and livers of the test subjects were investigated, and the uptake in each organ was counted in a dose calibrator. The $^{99m}$Tc-choline radioactivity uptake in these organs was significantly greater (p<0.001) than the uptake of the $^{99m}TcO_4$ controls. Uptake in the liver was found to be the highest uptake for the [methyl]-choline chloride labeled with $^{99m}TcO_4$. Thus, in addition to usage as a cancer detecting agent, the radioimaging agent is also particularly effective in imaging the liver.

It is to be understood that the present invention is not limited to the embodiment described above, but encompasses any and all embodiments within the scope of the following claims.

I claim:

1. A cancer-imaging agent, comprising [methyl]-choline chloride labeled with technetium-99m.

2. A cancer-imaging agent comprising choline or a pharmaceutically acceptable salt thereof labeled with technetium-99m.

3. A method of detecting cancer in a patient, comprising the steps of:
    injecting the patient with an effective amount of a radioimaging agent comprising choline or a pharmaceutically acceptable salt thereof labeled with tecnetium-99m;
    scanning the patient with a radioimaging device; and
    identifying cancerous tissue in areas where the scanning shows increased uptake of choline.

4. The method of detecting cancer as recited in claim 3, wherein the choline labeled with technetium-99m was prepared by labeling [methyl]-choline chloride with $^{99m}TcO_4$.

5. The method of detecting cancer as recited in claim 4, wherein said scanning step further comprises scanning the patient's liver with the radioimaging device.

6. The method of detecting cancer as recited in claim 3, wherein said scanning step further comprises scanning the patient's liver with the radioimaging device.

7. The method of detecting cancer as recited in claim 3, wherein said scanning step further comprises imaging selected soft tissue areas of the patient's body for increased choline uptake.

* * * * *